(12) United States Patent
Chang et al.

(10) Patent No.: US 8,012,157 B2
(45) Date of Patent: Sep. 6, 2011

(54) INTERNAL BONE FIXATION SIZING DEVICE AND METHODS

(75) Inventors: Narissa Y. Chang, Mansfield, MA (US); Dennis P. Colleran, North Attleboro, MA (US); Robert A. Rabiner, Tiverton, RI (US); Justin G. Dye, Mansfield, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 388 days.

(21) Appl. No.: 12/339,244

(22) Filed: Dec. 19, 2008

(65) Prior Publication Data

US 2009/0171358 A1  Jul. 2, 2009

Related U.S. Application Data

(60) Provisional application No. 61/017,367, filed on Dec. 28, 2007.

(51) Int. Cl.
*A61B 17/58* (2006.01)
*A61B 17/60* (2006.01)
*A61F 2/00* (2006.01)

(52) U.S. Cl. .............. 606/102; 606/62; 606/63; 606/95; 606/86 R; 128/898

(58) Field of Classification Search ............. 606/62, 606/63, 95, 167–175, 205–208, 79, 80, 86 R, 606/96, 102, 279, 329; 600/564–567; 128/898
See application file for complete search history.

(56) References Cited

U.S. PATENT DOCUMENTS

| | | | |
|---|---|---|---|
| 4,294,251 A | 10/1981 | Greenwald et al. | |
| 5,554,111 A | 9/1996 | Morrey et al. | |
| 5,707,374 A | 1/1998 | Schmidt | |
| 5,865,724 A * | 2/1999 | Palmer et al. ............... | 600/104 |
| 6,358,252 B1 | 3/2002 | Shapira | |
| 6,478,751 B1 | 11/2002 | Krueger et al. | |
| 7,806,900 B2 | 10/2010 | Rabiner | |
| 7,811,284 B2 | 10/2010 | Rabiner et al. | |
| 2006/0068362 A1 | 3/2006 | Desrosiers et al. | |
| 2007/0106181 A1 | 5/2007 | Mangiardi et al. | |
| 2008/0039854 A1 | 2/2008 | Rabiner | |
| 2008/0125784 A1 | 5/2008 | Rabiner et al. | |

* cited by examiner

*Primary Examiner* — Eduardo C Robert
*Assistant Examiner* — Christina Negrelli
(74) *Attorney, Agent, or Firm* — Greenberg Traurig, LLP; David J. Dykeman; Danielle T. Abramson

(57) ABSTRACT

An internal bone fixation sizing device and methods for using this device during a procedure for repairing a weakened or fractured bone are disclosed herein. A medical device for determining a depth and a diameter of a medullary cavity of a bone includes an outer shaft having a proximal end engaging an activation mechanism, a distal end having a first opening at an upper surface and a second opening at a lower surface, and a longitudinal axis between the proximal end and the distal end, wherein the longitudinal axis of the outer shaft includes a plurality of markers; and an inner shaft having a proximal end engaging the activation mechanism, a distal end terminating in two sizing arms, and a longitudinal axis therebetween, wherein the two sizing arms are able to move from a retracted position to an extended position extending beyond the outer shaft.

20 Claims, 7 Drawing Sheets

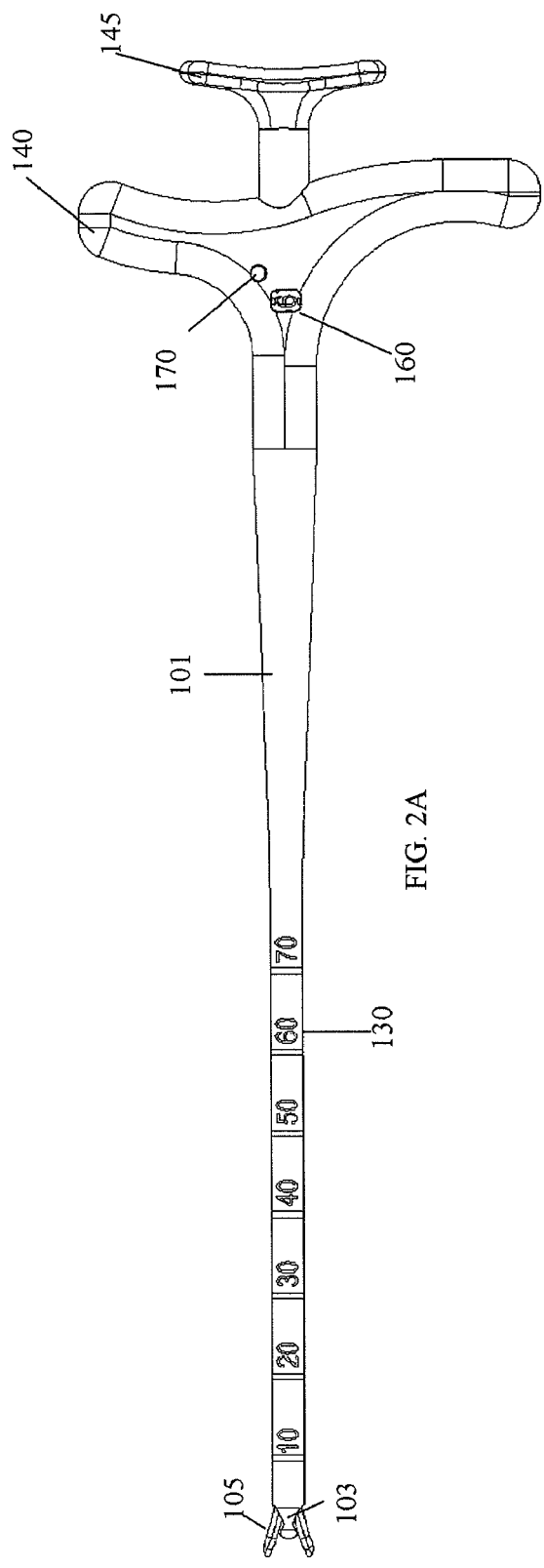
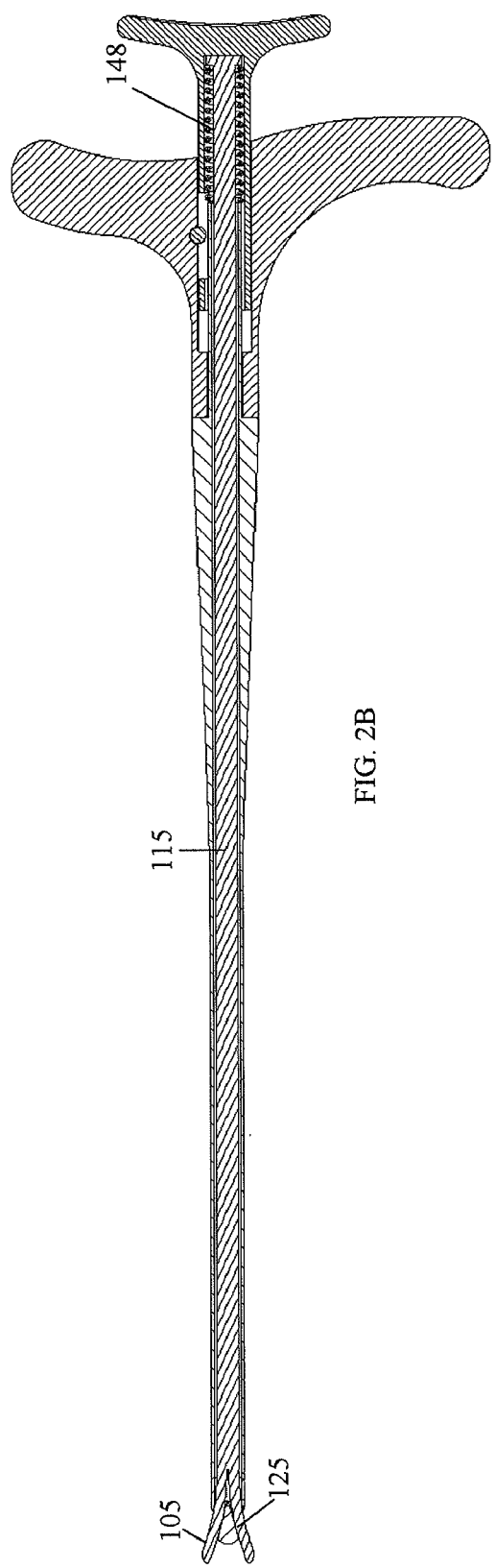
FIG. 2A
FIG. 2B

INTERNAL BONE FIXATION SIZING DEVICE AND METHODS

RELATED APPLICATIONS

This application is related to and claims the benefit of priority from U.S. Provisional Patent Application No. 61/017,367, filed on Dec. 28, 2007, the entirety of which is incorporated herein by reference.

FIELD

The embodiments disclosed herein relate to a medical device for use during an internal bone fixation procedure, and more particularly to an internal bone fixation sizing device and methods of using the sizing device for preparing and sizing a medullary cavity of a fractured bone for a bone fixation pin.

BACKGROUND

Bone is a living tissue and plays a structural role in the body. A bone fracture is a medical condition in which a bone has cracked or broken. While many fractures are the result of high force impact or stress, bone fracture can also occur as a result of certain medical conditions that weaken the bones, such as osteoporosis, certain types of cancer or osteogenesis imperfecta. The average person sustains two to three fractured bones during the course of a lifetime. Fracture repair is the process of rejoining and realigning the ends of broken bones. Currently there are several internal approaches to repair, strengthen and support a fractured bone.

Conventional internal fixation devices include wires, plates, rods, pins, nails, and screws to support the fractured bone directly, as well as the addition of bone cement mixtures, or bone void fillers to the fractured bone. For example, one common device includes a thick rod, or a plurality of thinner rods, which are implanted into the medullary cavity of the broken bone to stabilize the placement of the bone fragments once they are set in place. In order for these rods to function properly upon implantation, however, they must fit tightly within the medullary cavity. This fit is usually achieved by boring or reaming the cavity to obtain a constant diameter, widened cavity in which the rod is inserted.

Newer internal fixation devices include expandable members in which an outer surface of the device contacts the interior surface of the medullary cavity which leads to greater support and strength to the healing bone. Drawbacks to the present techniques for using these expandable members include the guess work involved in fitting the expandable member within the medullary cavity available. For example, since a medical professional cannot see into the cavity space, there is a lack of knowledge as to the size of the available space in the cavity and the exact pressure needed to expand the member. If too much pressure is exerted on the expandable member, necrosis of bone along the entire length of the fractured bone is possible. Also, since most of the expandable members presently available are pre-sized, an expandable member that does not conform to the cavity space available may be used, resulting in an improper fixation of the fractured bone and poor healing.

Therefore, there is a need in the art for a device that can be used prior to inserting an expandable member within the medullary cavity space that can predict the size of the cavity. This pre-procedure sizing will enable custom fit bone fixation pins and lead to advantageous healing conditions.

SUMMARY

A sizing device and method of using the sizing device for preparing and sizing a medullary cavity of a fractured bone for a custom fit bone fixation pin are disclosed herein. According to aspects illustrated herein, there is provided a medical device for determining a length and a diameter of a medullary cavity of a bone that includes an outer shaft having a proximal end engaging an activation mechanism, a distal end having a first opening at an upper surface and a second opening at a lower surface, and a longitudinal axis between the proximal end and the distal end, wherein the longitudinal axis of the outer shaft includes a plurality of markers; and an inner shaft having a proximal end engaging the activation mechanism, a distal end terminating in two sizing arms, and a longitudinal axis therebetween, wherein the two sizing arms are able to move from a retracted position to an extended position extending beyond the outer shaft.

According to aspects illustrated herein, there is provided a method for determining a depth and a diameter of a cleared-out medullary cavity of a bone that includes gaining access to the medullary cavity of the bone; removing medullary material from the medullary cavity to form a void in the bone; providing a medical device, the medical device including: an outer shaft having a proximal end engaging an activation mechanism, a distal end having a first opening at an upper surface and a second opening at a lower surface, and a longitudinal axis between the proximal end and the distal end, wherein the longitudinal axis of the outer shaft includes a plurality of markers; and an inner shaft having a proximal end engaging the activation mechanism, a distal end terminating in two sizing arms, and a longitudinal axis therebetween, wherein the two sizing arms are able to move from a retracted position to an extended position extending beyond the outer shaft; inserting the medical device into the void; determining the depth of the void by viewing the radiopaque markers on the outer shaft of the device; activating the activation mechanism to move the two sizing arms from the retracted position into the extended position; and determining a first diameter dimension of the void by reading a readout from a window in the activation mechanism.

According to aspects illustrated herein, there is provided a method for clearing excess medullary material from a void in a bone that includes gaining access to the medullary cavity of the bone through an access hole; removing initial medullary material from the medullary cavity to form the void in the bone; providing a medical device, the medical device including: an outer shaft having a proximal end engaging an activation mechanism, a rounded distal end having a first opening at an upper surface and a second opening at a lower surface, and a longitudinal axis between the proximal end and the distal end; and an inner shaft having a proximal end engaging the activation mechanism, a distal end terminating in two sizing arms, and a longitudinal axis therebetween, wherein the two sizing arms move from a retracted position to an extended position extending beyond the outer shaft through the first opening at the upper surface and the second opening at the lower surface of the distal end; inserting the medical device into the void in the bone, wherein the two sizing arms of the medical device are in the retracted position; and moving the medical device within the void to clear excess medullary material within the void.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A shows an internal bone fixation sizing device with two sizing arms in a retracted or "bone sound" position. FIG. 1B shows an internal bone fixation sizing device with two sizing arms in an extended position.

FIG. 2A and FIG. 2B show side views of an internal bone fixation sizing device according to the presently disclosed embodiments. FIG. 2A shows some of the main outer components of the device. FIG. 2B is a cross-sectional view showing some of the main internal components of the device.

FIG. 3A shows a head portion of the distal end of the device in a retracted or "bone sound" position. FIG. 3B shows the head portion of the distal end of the device in an extended "bone measurement" position.

FIG. 4A shows the device positioned within the medullary cavity of the fractured bone. FIG. 4B is a cross-sectional view showing some of the main internal components of the device positioned within the medullary cavity of the fractured bone.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

A medical device and methods for using this device during an internal bone fixation procedure are disclosed herein. The medical device acts as a sizing device and is used for preparing and sizing a medullary cavity of a fractured bone for a custom fit bone fixation pin. The sizing device enables a user to complete several tasks, which include clearing any residual medullary material from the medullary cavity of the fractured bone prior to insertion of a custom fit bone fixation pin, determining the depth of the medullary cavity prior to insertion of a custom fit bone fixation pin, and measuring the diameter of the medullary cavity prior to insertion of the custom fit bone fixation pin. Knowing the measurements of the medullary cavity prior to insertion of a bone fixation pin provides a customized pin for the fractured bone which results in an internal bone fixation pin.

Figure 1A:
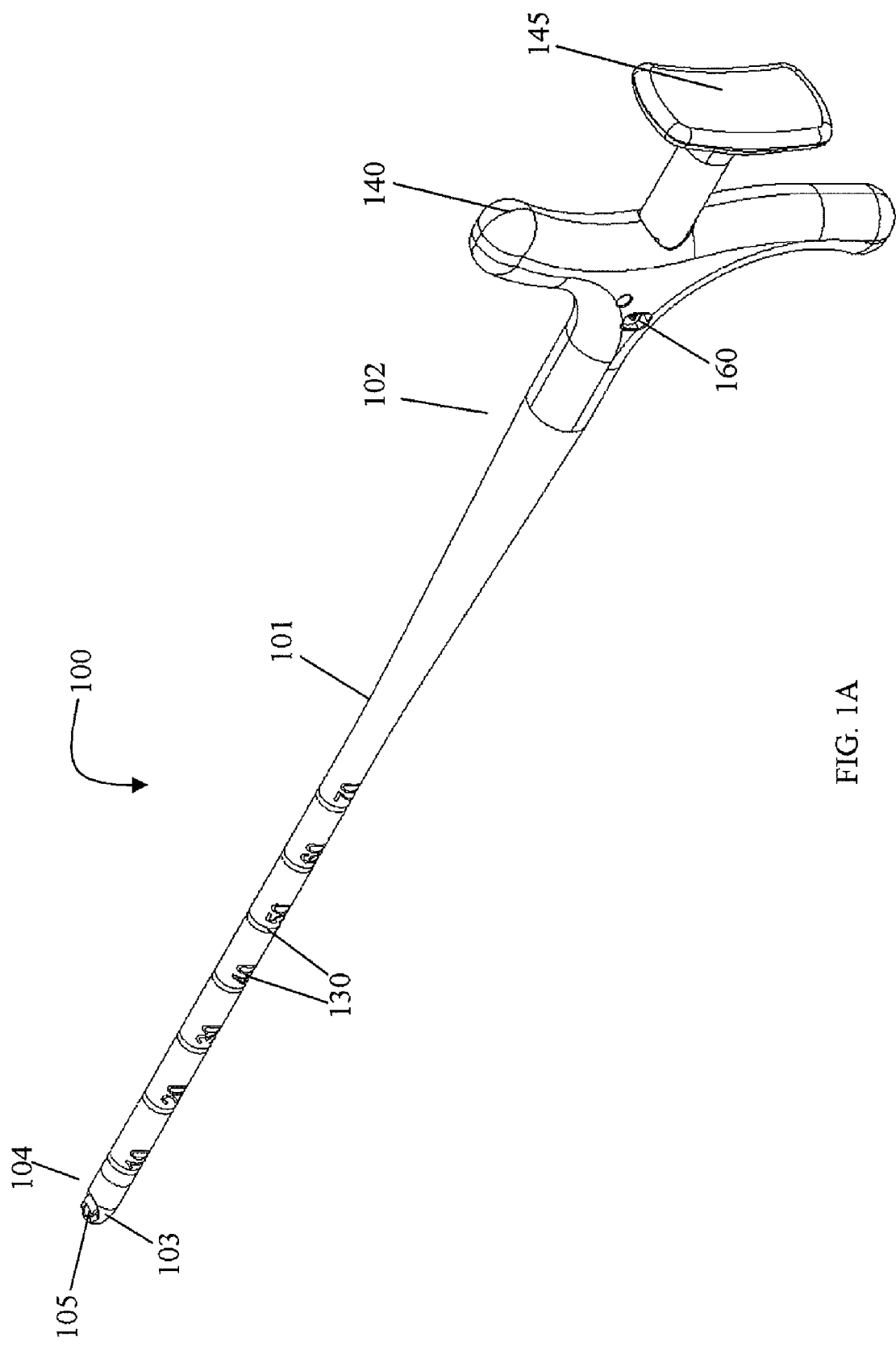
FIG. 1A and FIG. 1B show perspective views of an internal bone fixation sizing device for preparing and sizing a medullary cavity of a fractured bone for a custom fit bone fixation pin according to the presently disclosed embodiments.
Figure 1B:
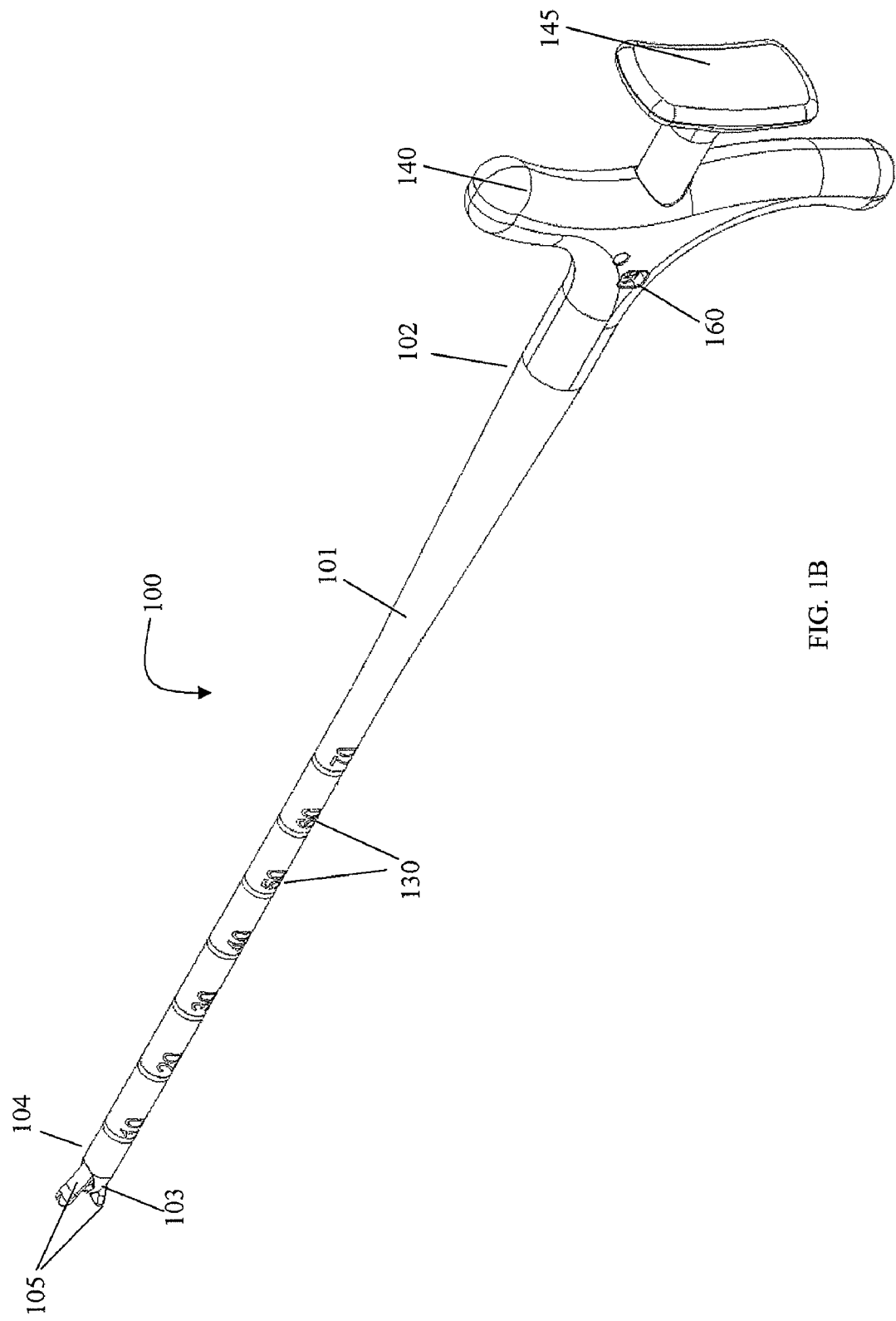

The main components of a sizing device 100 of the presently disclosed embodiments are shown generally in FIG. 1A and FIG. 1B in conjunction with FIG. 2A and FIG. 2B. The sizing device 100 includes an elongated shaft 101 with a proximal end 102, a distal end 104, and a longitudinal axis therebetween. The diameter of the elongated shaft 101 of the sizing device 100 may range from about 2 mm to about 4 mm or larger. In an embodiment, the elongated shaft 101 has a diameter of about 3 mm. The distal end 104 of the device 100 terminates in a head portion 103. In an embodiment, the head portion 103 is welded onto the elongated shaft 101 with techniques known in the art. Alternately, the head portion 103 and the elongated shaft 101 may be fabricated as a continuous piece. An arm shaft 115 housed within the body of the elongated shaft 101 terminates in two expandable sizing arms 105 at the distal end 104 of the device 100. Openings 116 at an upper surface and a lower surface of the head portion 103 allow for the sizing arms 105 to retract (as seen in FIG. 1A) and extend (as seen in FIG. 1B). As shown in FIG. 1A, the sizing arms 105 are in a retracted position within the head portion 103. In the retracted position, the sizing arms 105 are located inside the head portion 103, resting about 4 mm apart from one another. As can be seen in FIG. 2B, the sizing arms 105 extend by sliding up and down respective inclined surfaces 125 within the body of the elongated shaft 101.

The elongated shaft 101 of the device 100 is flexible, so that the device 100 may accommodate bends in the shape and geometry of a bone, allowing the distal end 104 of the device 100 to reach a desired location inside a bone. The outside surface of the elongated shaft 101 is marked with radiopaque markers 130, displaying depth indicators and numbers in millimeter dimensions. These radiopaque markers 130 allow a user to gauge the depth of a cleared-out medullary cavity of a fractured bone. The radiopaque markers 130, using radiopaque materials such as barium sulfate, tantalum, or other materials known to increase radiopacity, allow the user to view the device 100 using fluoroscopy techniques. A typical readout for the length of the medullary cavity may range from about 10 mm to about 70 mm or greater. In an embodiment, the sizing arms 105 are coated with a radiopaque material or contain radiopaque materials that are known to increase radiopacity, which will allow the user to view the sizing arms 105 using fluoroscopy techniques.

A handle 140 engages the proximal end 102 of the device 100 and allows for activation of an activation mechanism 145. In an embodiment, the activation mechanism 145 is a thumb press. The thumb press 145 activates a spring 148 located at a proximal end of the arm shaft 115, within the handle 140 housing, which pushes the arm shaft 115 forward. A spring pin 170 keeps the arm shaft 115, the spring 148, and the thumb press 145 housed within the handle 140 and controls the distance traveled by the spring 148. A window 160 machined into the handle 140 provides millimeter dimension readouts that reflect the inner diameter dimensions of the medullary cavity of the fractured bone. A typical readout for the diameter of the medullary cavity may range from about 4 mm to about 9 mm or greater. As seen in FIG. 2A, the readout in the window 160 is 6 mm. Alternately, other suitable activation mechanisms 145 can be used that are known in the art including, but not limited to, a trigger device, a threaded knob which translates rotational motion to linear motion, and mating gears.

Figure 3B:
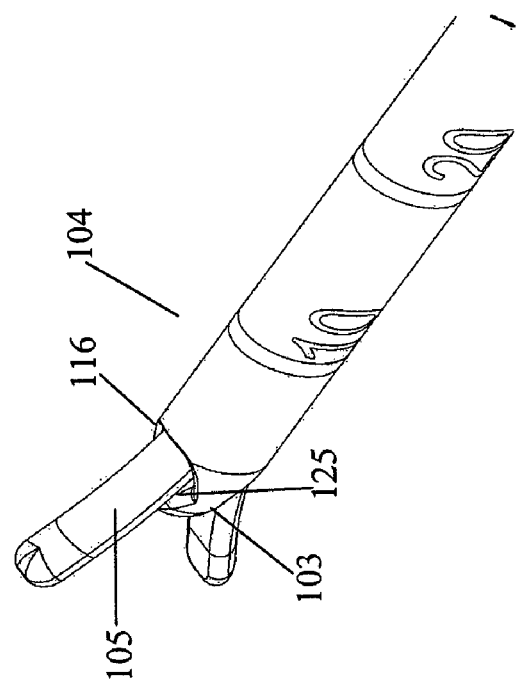
FIG. 3A and FIG. 3B show close-up perspective views of a distal end of an internal bone fixation sizing device according to the presently disclosed embodiments.
Figure 3A:
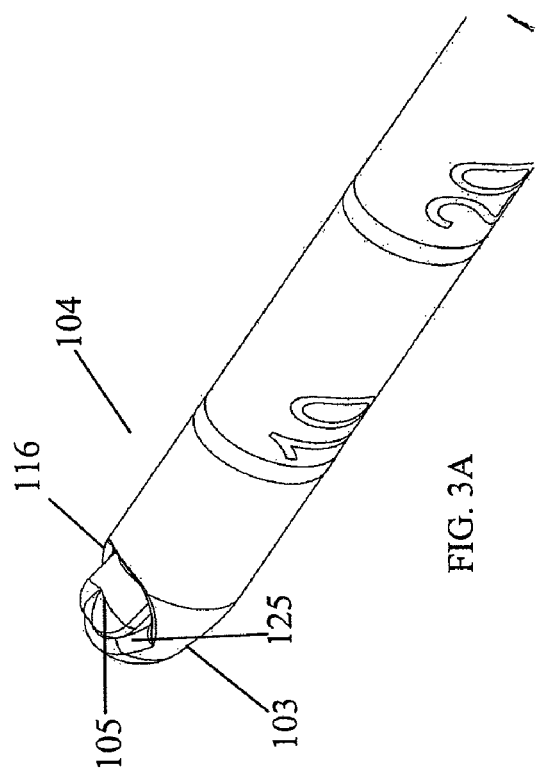

FIG. 3A and FIG. 3B show close-up perspective views of the distal end 104 of the internal bone fixation sizing device. The head portion 103 is rounded, allowing for smooth entry into a fractured bone void, i.e., a medullary cavity of a fractured bone. The head portion 103 has a gradual increase in diameter. The openings 116 at the head portion 103 allow for the sizing arms 105 to extend and retract. As shown in FIG. 3A, the sizing arms 105 are in a retracted position, also referred to as a "bone sound" position. In this retracted position, the sizing arms 105 rest about 4 mm apart along the inclined surfaces 125. When the sizing arms 105 are in the bone sound position, the rounded head portion 105 is able to clear away any residual medullary material that remains within the medullary cavity of the fractured bone. As the thumb press 145 is pushed, the arm shaft 115 moves forward within the interior of the elongated shaft 101, thus moving the sizing arms 105 up along the inclined surfaces 125. The sizing arms 105 extend through the openings 116 of the head portion 103 extending beyond the outer shaft 101, as shown in FIG. 3B. When the sizing arms 105 contact interior surfaces of the fractured bone void, the corresponding diameter dimensions are displayed within the window 160 of the handle 140. In an embodiment, the diameter dimensions are displayed in units of millimeters. Once the readout is determined or a desired measurement is achieved, the thumb press 145 is released, causing the sizing arms 105 to retract into the head portion 103 and return to the retracted position. At this time, the sizing device 100 may be removed from the void or re-positioned within the void in order to obtain another diameter dimension readout. For example, the sizing device 100 may be re-positioned within the void so that the sizing arms 105 are about perpendicular to a longitudinal axis of the void. After re-positioning, the thumb press 145 is pushed, the arm shaft 115 moves forward within the interior of the elongated shaft 101, and the sizing arms 105 are moved up along the inclined surfaces 125. The sizing arms 105 extend through the openings 116 of the head portion 103 and extend beyond the outer shaft 101. The sizing arms 105 contact the interior surfaces of the fractured bone void, and a corresponding diameter dimension is displayed within the window 160 of the handle 140. In this way, the sizing device 100 will be able to provide an overall picture of the internal geometry of the void.

The presently disclosed embodiments use minimally invasive approaches to gain access to a fractured bone. Minimally invasive refers to surgical means, such as microsurgical, endoscopic or arthroscopic surgical means, that can be accomplished with minimal disruption of the pertinent musculature, for instance, without the need for open access to the tissue injury site or through minimal incisions. Minimally invasive procedures are often accomplished by the use of visualization such as fiber optic or microscopic visualization, and provide a post-operative recovery time that is substantially less than the recovery time that accompanies the corresponding open surgical approach. Benefits of minimally invasive procedures include causing less trauma because there is minimal blood loss, a reduction in surgery and anesthetized time, shortened hospitalization, and an easier and more rapid recovery.

Figure 4A:
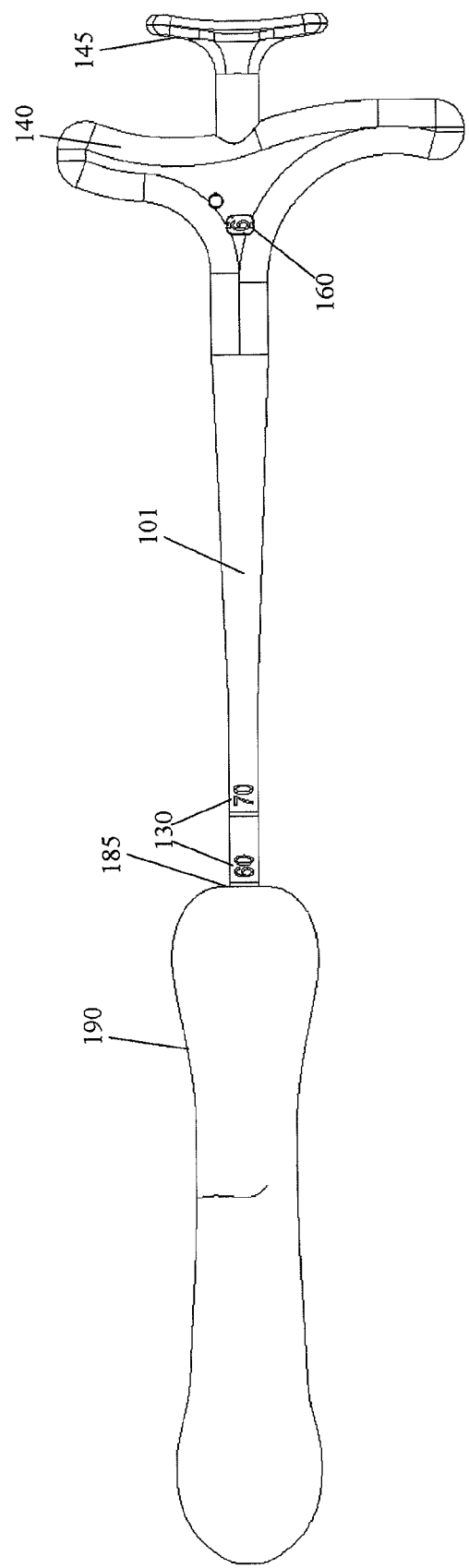
FIG. 4A and FIG. 4B show side views of an internal bone fixation sizing device positioned within a medullary cavity of a fractured bone according to the presently disclosed embodiments.
Figure 4B:
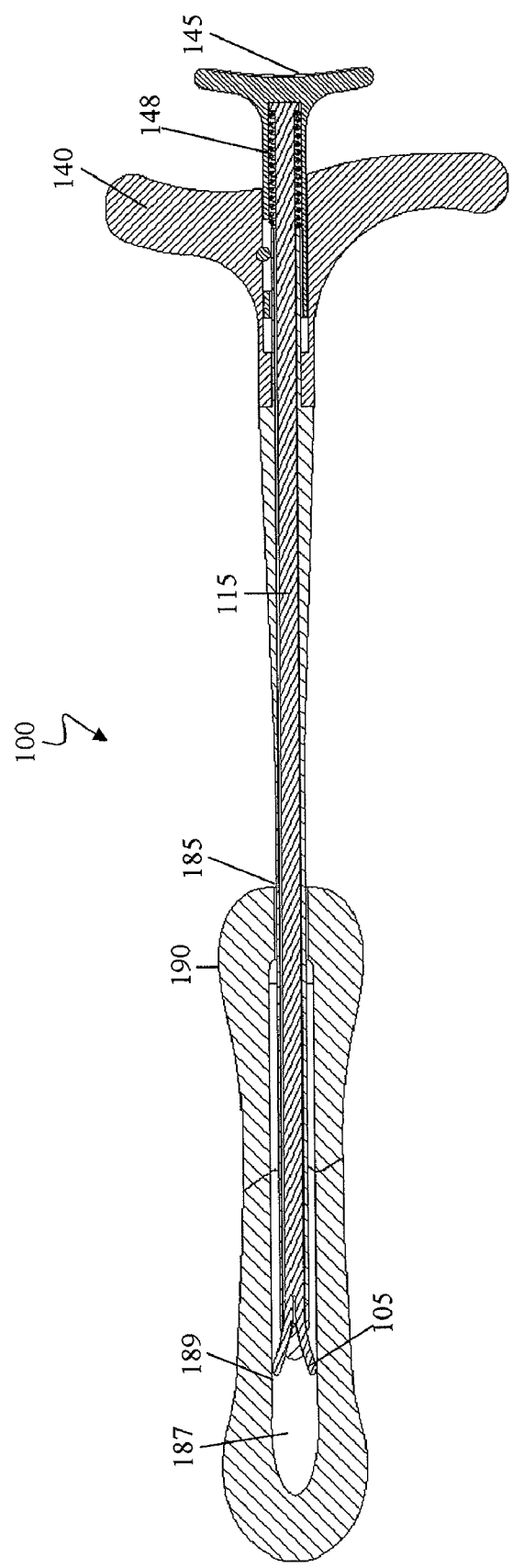

FIG. 4A and FIG. 4B show side views of the internal bone fixation sizing device 100 in place within a fractured bone 190. For simplicity, surrounding tissue and bones are not shown in FIG. 4A and FIG. 4B. A method of placing the device 100 within a medullary cavity of the fractured bone 190 includes making a minimally invasive incision (not shown) through a patient's skin to expose the fractured bone 190. The incision may be made at the proximal end or the distal end of the fractured bone 190 to expose the bone surface. Once the bone 190 is exposed, it may be necessary to retract some muscles and tissues that may be in view of the fractured bone 190. An access hole 185 is formed in the fractured bone 190 by drilling or other methods known in the art. The diameter of the access hole 185 is determined based on the size of the fractured bone 190 and the diameter of a bone fixation pin. The access hole 185 extends through a hard compact outer cortical layer of the fractured bone 190 into the relatively porous inner or cancellous bone. For fractured bones 190 with marrow, medullary material including air, blood, fluids, fat, marrow, tissue and bone debris, should be cleared from the medullary cavity to form a void 187. The void 187 is defined as a hollowed out space, wherein a first position defines the most distal edge of the void 187 with relation to the access hole 185 on the fractured bone 190, and a second position defines the most proximal edge of the void 187 with relation to the access hole 185 on the fractured bone 190. The fractured bone 190 may be hollowed out sufficiently to have the medullary material of the medullary cavity up to the cortical bone removed. There are many methods for removing the medullary material that are known in the art and within the spirit and scope on the presently disclosed embodiments including, but not limited to, methods described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

The internal bone fixation sizing device 100 is introduced into the void 187 of the fractured bone 190 via the access hole 185. Initially, the sizing device 100 is inserted into the void 187 without activating the thumb press 145, so that the sizing arms 105 remain in the bone sound or retracted position. The sizing device 100 is inserted into the void 187 and may be moved back and forth within the void 187, allowing the surfaces of the head portion 103 and the sizing arms 105 to break off and push away any excess medullary material that may otherwise block the path of an internal bone fixation pin. In an embodiment, the thumb press 145 is activated, causing the sizing arms 105 to extend through the openings 116 of the head portion 103. The sizing arms 105, in this extended position may be moved back and forth within the void 187, allowing the surfaces of the head portion 103 and the extended sizing arms 105 to break off and push away any excess medullary material that may otherwise block the path of the internal bone fixation pin. Once the void 187 has been cleared-out of excess medullary material, measurements of the interior of the void 187 may be gauged. Fluoroscopic images may be taken incrementally, allowing a user to gradually gauge the depth of the void 187 using the radiopaque markers 130, until the head portion 103 of the sizing device 100 has reached a desired location within the void 187. The thumb press 145 of the sizing device 100 may or may not be activated throughout this procedure. The radiopaque markers 130 on the outside of the device 100 provide a measurement of the approximate depth of the void 187, providing detailed information on the approximate length requirements for the bone fixation pin needed to support the fractured bone.

Figure 5:
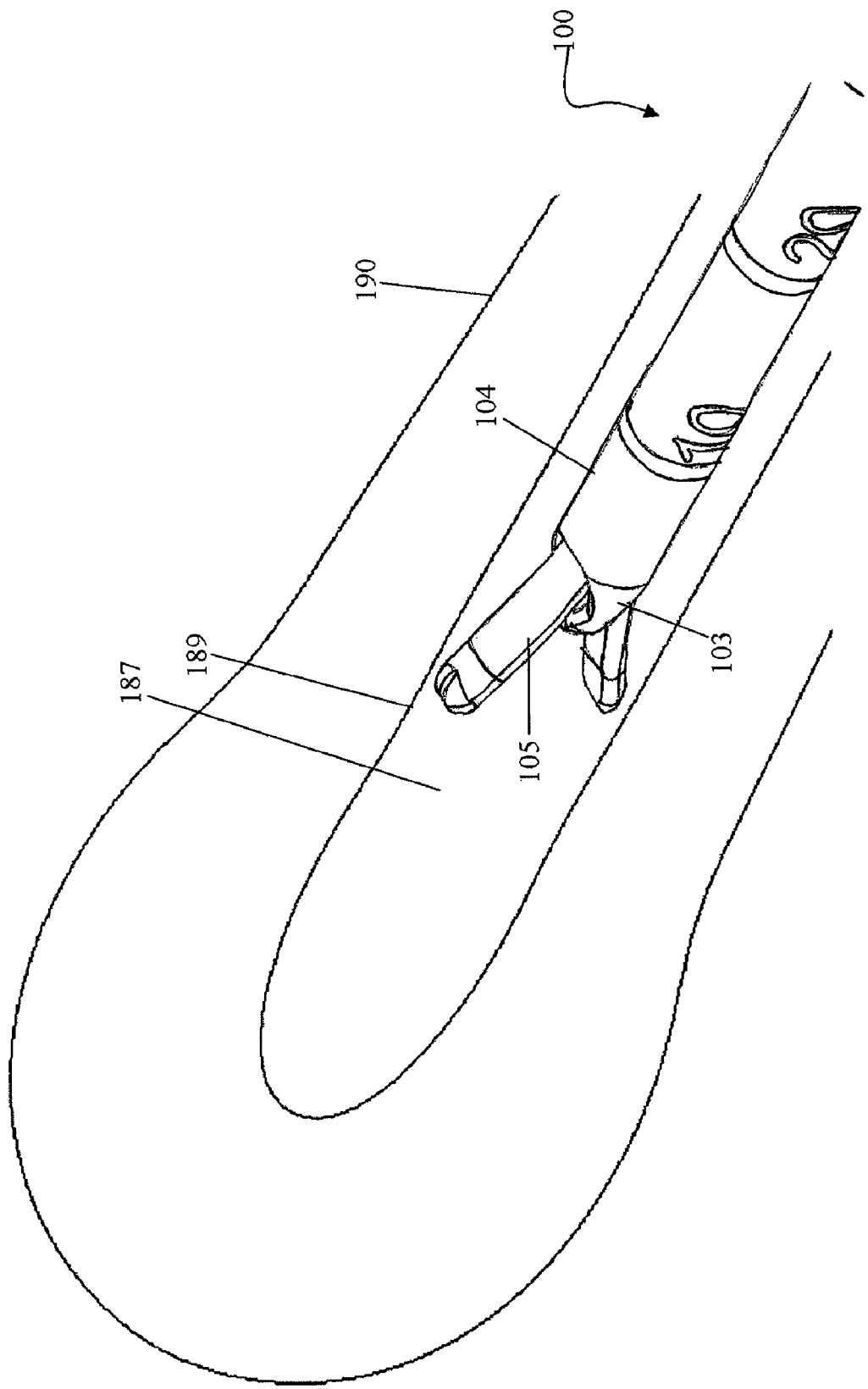
FIG. 5 shows a close-up perspective view of an internal bone fixation sizing device bone in a bone measurement position within the medullary cavity of the fractured bone according to the presently disclosed embodiments.

By activating the thumb press 145, the spring 148 pushes the arm shaft 115 forward causing the sizing arms 105 to extend from the openings 116 of the head portion 103. The sizing arms 105 extend and expand to contact an interior surface 189 of the bone void 187. A corresponding diameter measurement readout will be provided through the window 160 on the handle 140. Once the readout has been determined, or a desired diameter measurement has been achieved, the thumb press 145 is released, causing the sizing arms 105 to retract within the device 100. FIG. 5 shows a close-up perspective view of the distal end 104 of the device 100 within the void 187 of the fractured bone 190. As shown in FIG. 5, the sizing arms 105 have been extended through the openings 116 and contact the interior surface 189 of the void 187. The sizing device 100 may be re-positioned within the void 187 in order to obtain another diameter dimension readout. In an embodiment, the sizing device 100 is re-positioned within the void so that the sizing arms 105 are about perpendicular to a longitudinal axis of the void. In an embodiment, the sizing device 100 is re-positioned along the depth of the void. After re-positioning, the thumb press 145 is pushed, the arm shaft 115 moves forward within the interior of the elongated shaft 101, and the sizing arms 105 are moved up along the inclined surfaces 125. The sizing arms 105 extend through the openings 116 of the head portion 103 and extend beyond the outer shaft 101. The sizing arms 105 contact the interior surfaces of the fractured bone void, and a corresponding diameter dimension is displayed within the window 160 of the handle 140. In this way, the sizing device 100 will be able to provide an overall picture of the internal geometry of the void 187.

The internal bone fixation sizing device and methods disclosed herein can be used prior to the insertion of an internal bone fixation device. Internal bone fixation devices are known in the art. Examples of internal bone fixation devices that may be used in conjunction with the sizing device disclosed herein include, but are not limited to, those devices described in U.S. patent application Ser. No. 11/789,907 entitled "Apparatus and Method for Delivery of Reinforcing Materials to Bone" and U.S. patent application Ser. No. 11/903,123 entitled "Systems and Methods for Internal Bone Fixation."

A method for determining a depth and a diameter of a cleared-out medullary cavity of a bone according to the presently disclosed embodiments includes gaining access to the medullary cavity of the bone; removing medullary material from the medullary cavity to form a void in the bone; providing a medical device, the medical device including: an outer shaft having a proximal end engaging an activation mechanism, a distal end having a first opening at an upper surface and a second opening at a lower surface, and a longitudinal axis between the proximal end and the distal end, wherein the longitudinal axis of the outer shaft includes a plurality of radiopaque markers; and an inner shaft having a proximal end engaging the activation mechanism, a distal end terminating in two sizing arms, and a longitudinal axis therebetween, wherein the two sizing arms are able to move from a retracted position to an extended position extending beyond the outer shaft; inserting the medical device into the void; determining the depth of the void by viewing the radiopaque markers on the outer shaft of the device; activating the activation mechanism to move the two sizing arms from the retracted position into the extended position; and determining a first diameter dimension of the void by reading a readout from a window in the activation mechanism.

A method for clearing excess medullary material from a void in a bone that includes gaining access to the medullary cavity of the bone through an access hole; removing initial medullary material from the medullary cavity to form the void in the bone; providing a medical device, the medical device including: an outer shaft having a proximal end engaging an activation mechanism, a rounded distal end having a first opening at an upper surface and a second opening at a lower surface, and a longitudinal axis between the proximal end and the distal end; and an inner shaft having a proximal end engaging the activation mechanism, a distal end terminating in two sizing arms, and a longitudinal axis therebetween, wherein the two sizing arms move from a retracted position to an extended position extending beyond the outer shaft through the first opening at the upper surface and the second opening at the lower surface of the distal end; inserting the medical device into the void in the bone, wherein the two sizing arms of the medical device are in the retracted position; and moving the medical device within the void to clear excess medullary material within the void.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A medical device for determining a depth and a diameter of a medullary cavity of a bone comprising:
  an outer shaft having:
    a proximal end engaging an activation mechanism,
    a distal end having a first opening at an upper surface and a second opening at a lower surface, and a longitudinal axis between the proximal end and the distal end, wherein the longitudinal axis of the outer shaft includes a plurality of markers for determining the depth of the medullary cavity of the bone;
  an inner shaft having a proximal end engaging the activation mechanism, a distal end terminating in two sizing arms, and a longitudinal axis therebetween,
    wherein the two sizing arms are moveable through the first opening and the second opening of the distal end of the outer shaft from a retracted position in which the two sizing arms are located inside the outer shaft to an extended position in which the two sizing arms extend beyond the distal end of the outer shaft; and
  a diameter dimension readout reflecting a spaced apart distance between the two sizing arms when the two sizing arms are in the extended position for determining the diameter of the medullary cavity of the bone.

2. The medical device of claim 1 wherein the plurality of markers are circumferential rings spaced apart uniformly along the outer shaft.

3. The medical device of claim 1 wherein the plurality of markers are numeric indicia spaced apart starting from the distal end of the outer shaft.

4. The medical device of claim 1 wherein the plurality of markers are radiopaque.

5. The medical device of claim 1 wherein the activation mechanism includes a handle and a thumb press.

6. The medical device of claim 5 wherein activation of the thumb press causes a spring at the proximal end of the inner shaft to push the inner shaft in a forward movement.

7. The medical device of claim 6 wherein the inner shaft moving forward causes the two sizing arms to move from the retracted position to the extended position so that the two sizing arms protrude from the first opening and the second opening of the distal end.

8. The medical device of claim 1 further comprising a window in a handle for viewing the diameter dimension readout.

9. The medical device of claim 1 wherein the distal end is rounded to allow smooth entry into the medullary cavity of the bone.

10. The medical device of claim 1 wherein the outer shaft is flexible to accommodate bends in the bone.

11. The medical device of claim 1 wherein the two sizing arms contain radiopaque material.

12. A method for determining a depth and a diameter of a cleared-out medullary cavity of a bone comprising:
  gaining access to the medullary cavity of the bone;
  removing medullary material from the medullary cavity to form a void in the bone;

providing a medical device, the medical device including:
an outer shaft having a proximal end engaging an activation mechanism, a distal end having a first opening at an upper surface and a second opening at a lower surface, and a longitudinal axis between the proximal end and the distal end, wherein the longitudinal axis of the outer shaft includes a plurality of markers; and
an inner shaft having a proximal end engaging the activation mechanism, a distal end terminating in two sizing arms, and a longitudinal axis therebetween, wherein the two sizing arms are able to move from a retracted position to an extended position extending beyond the outer shaft;
inserting the medical device into the void in the bone;
determining the depth of the void by viewing the markers on the outer shaft of the device;
activating the activation mechanism to move the two sizing arms from the retracted position into the extended position; and
determining a first diameter dimension of the void by reading a readout from a window in the activation mechanism.

13. The method of claim 12 wherein the plurality of markers are numeric indicia spaced apart starting from the distal end of the outer shaft.

14. The method of claim 12 wherein the plurality of markers are radiopaque.

15. The method of claim 12 wherein the distal end is rounded to allow smooth entry into the medullary cavity of the bone.

16. The method of claim 12 wherein the outer shaft is flexible to accommodate bends in the bone.

17. The method of claim 12 wherein the two sizing arms contain radiopaque material.

18. The method of claim 12 further comprising:
de-activating the activation mechanism to move the two sizing arms from the extended position into the retracted position;
repositioning the medical device within the void;
activating the activation mechanism to move the two sizing arms from the retracted position into the extended position; and
determining a second diameter dimension of the void by reading readout from the window in the activation mechanism,
wherein the first diameter reading and the second diameter reading provide a circumferential analysis of the diameter of the void.

19. A method for clearing excess medullary material from a void in a bone comprising:
gaining access to the medullary cavity of the bone through an access hole;
removing initial medullary material from the medullary cavity to form the void in the bone;
providing a medical device, the medical device including:
an outer shaft having a proximal end engaging an activation mechanism, a rounded distal end having a first opening at an upper surface and a second opening at a lower surface, and a longitudinal axis between the proximal end and the distal end; and
an inner shaft having a proximal end engaging the activation mechanism, a distal end terminating in two sizing arms, and a longitudinal axis therebetween,
wherein the two sizing arms move from a retracted position where the two sizing arms are located inside the outer shaft to an extended position where the two sizing arms extend beyond the distal end of the outer shaft through the first opening at the upper surface and the second opening at the lower surface of the distal end;
inserting the medical device into the void in the bone, wherein the two sizing arms of the medical device are in the retracted position; and
moving the medical device within the void to clear excess medullary material within the void.

20. The method of claim 19 further comprising activating the activation mechanism to move the two sizing arms from the retracted position into the extended position extending beyond the outer shaft through the first opening at the upper surface and the second opening at the lower surface of the distal end.

* * * * *